United States Patent
Yan et al.

(10) Patent No.: US 12,161,490 B2
(45) Date of Patent: Dec. 10, 2024

(54) METHOD FOR DETERMINING TUBE ELECTRICAL PARAMETERS, HOST DEVICE, AND IMAGING SYSTEM

(71) Applicant: OUR UNITED CORPORATION, Xi'an (CN)

(72) Inventors: Hao Yan, Xi'an (CN); Shaojie Chang, Xi'an (CN); Dalin Liu, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 292 days.

(21) Appl. No.: 17/731,682

(22) Filed: Apr. 28, 2022

(65) Prior Publication Data

US 2022/0346740 A1 Nov. 3, 2022

(30) Foreign Application Priority Data

Apr. 28, 2021 (CN) .......................... 202110466184.0

(51) Int. Cl.
*A61B 6/03* (2006.01)
*A61B 6/00* (2006.01)
*G06T 11/00* (2006.01)

(52) U.S. Cl.
CPC ............ *A61B 6/032* (2013.01); *A61B 6/5258* (2013.01); *G06T 11/008* (2013.01); *G06T 2210/41* (2013.01)

(58) Field of Classification Search
CPC ...... A61B 6/5258; A61B 6/032; G06T 11/008
See application file for complete search history.

(56) References Cited

U.S. PATENT DOCUMENTS

| | | | | |
|---|---|---|---|---|
| 5,680,427 | A * | 10/1997 | Dobbs ..................... | H05G 1/60 378/19 |
| 2003/0097062 | A1* | 5/2003 | Toth ....................... | A61B 6/465 600/425 |
| 2004/0032928 | A1* | 2/2004 | Toth ....................... | A61B 6/544 378/108 |
| 2012/0114093 | A1* | 5/2012 | Yu .......................... | A61B 6/481 378/8 |
| 2014/0177788 | A1* | 6/2014 | Stevens .................. | A61B 6/542 378/16 |
| 2014/0254748 | A1* | 9/2014 | Funk ..................... | G01N 23/046 378/19 |
| 2017/0010224 | A1* | 1/2017 | Thibault ................. | G06T 3/10 |
| 2017/0221234 | A1* | 8/2017 | Chen ..................... | G06T 5/50 |
| 2019/0099148 | A1* | 4/2019 | Rupcich ................ | H05G 1/265 |
| 2019/0239839 | A1* | 8/2019 | Rowley Grant ....... | A61B 6/544 |
| 2021/0082161 | A1* | 3/2021 | Cao ........................ | G06T 11/006 |

* cited by examiner

*Primary Examiner* — Hugh Maupin
(74) *Attorney, Agent, or Firm* — Knobbe, Martens, Olson & Bear, LLP (57) ABSTRACT

Provided is a method for determining tube electrical parameters. The method includes: acquiring target projection data of an imaging device in scanning a target object at a first scan angle; acquiring target noise data corresponding to the target object; determining current noise data corresponding to the target projection data; and determining, based on the target noise data and the current noise data, the tube electrical parameters of the imaging device in scanning the target object at a second scan angle.

15 Claims, 3 Drawing Sheets

METHOD FOR DETERMINING TUBE ELECTRICAL PARAMETERS, HOST DEVICE, AND IMAGING SYSTEM

CROSS-REFERENCE TO RELATED DISCLOSURE

The present disclosure claims priority to Chinese Patent Application No. 202110466184.0 filed on Apr. 28, 2021 and entitled "METHOD FOR DETERMINING TUBE ELECTRICAL PARAMETERS HOST DEVICE AND MEDICAL IMAGING SYSTEM" and the content of which is herein incorporated by reference in its entirely.

TECHNICAL FIELD

The present disclosure relates to a method for determining tube electrical parameters, a host device, and an imaging system.

BACKGROUND

Medical images contain a large amount of information of the human body, and can intuitively present functions of structures, morphology or visceral organ of the human internal tissue. Thus, medical imaging has become one of the most active fields in medical research and clinical diagnostic. Medical imaging technology, as a research direction in the field of the medical imaging, is a product of interpenetration of the advanced technologies such as physics, electronic technology, computer technology, engineering data, material science and fine processing, and the like.

According to information carrier, the medical imaging technology may be divided into x-ray imaging, magnetic resonance imaging, nuclide imaging, and ultrasound imaging, and the like. In an x-ray imaging system, with a fixed tube voltage and tube current, x-ray from an x-ray tube penetrates through an affected part of the body of the patient to reconstruct and scan affected part of the body of the patient.

SUMMARY

Embodiments of the present disclosure provide a method for determining tube electrical parameters, a host device, and an imaging system.

In a first aspect, a method for determining tube electrical parameters is provided. The method includes:
acquiring target projection data of an imaging device in scanning a target object at a first scan angle;
acquiring target noise data corresponding to the target object;
determining current noise data corresponding to the target projection data; and determining, based on the target noise data and the current noise data, the tube electrical parameters of the imaging device in scanning the target object at a second scan angle.

In a second aspect, a method for determining tube electrical parameters is provided. The method includes:
acquiring a second correspondence relationship with respect to a target object, wherein the second correspondence relationship includes a correspondence relationship between a scan angle and the tube electrical parameters; and
determining the tube electrical parameters corresponding to any scan angle in the second correspondences relationship as the tube electrical parameters of a first imaging device in scanning the target object at the any scan angle.

In a third aspect, an apparatus for determining tube electrical parameters is provided. The apparatus includes:
a first acquiring unit configured to acquire target projection data of an imaging device in scanning a target object at a first scan angle;
a second acquiring unit configured to acquire target noise data corresponding to the target object;
a determining unit configured to determine current noise data corresponding to the target projection data; and
an adjusting unit configured to determine, based on the target noise data and the current noise data, the tube electrical parameters of the imaging device in scanning the target object at a second scan angle.

In a fourth aspect, an apparatus for determining tube electrical parameters is determined. The apparatus includes:
an acquiring unit configured to acquire a second correspondence relationship with respect to a target object, wherein the second correspondence relationship includes a correspondence relationship between a scan angle and the tube electrical parameters; and
a determining unit configured to determine the tube electrical parameters corresponding to any scan angle in the second correspondences relationship as the tube electrical parameters of a first imaging device in scanning the target object at the any scan angle.

In a fifth aspect, a host device is provided. The host device includes:
one or more processors;
a memory configured to store one or more computer programs therein; and
wherein the one or more processors, when loading and running the one or more computer programs, are caused to perform the method according to any one of the first aspect, the embodiments of the first aspect, the second aspect, and the embodiments of the second aspect.

In a sixth aspect, a non-transitory computer-readable storage medium is provided. The computer-readable storage medium stores a computer program therein, wherein the one or more computer programs, when loaded and run by a processor of an electronic device, causes the electronic device to perform the method according to any one of the first aspect, the embodiments of the first aspect, the second aspect, and the embodiments of the second aspect.

In a seventh aspect, an imaging system is provided. The imaging system includes a host device and an imaging device, wherein the host device is communicatively connected to the imaging device, and the host device is the host device according to the fourth aspect.

DETAILED DESCRIPTION

The technical solutions of the present disclosure are described in detail hereinafter in combination with the accompanying drawings. The embodiments described hereinafter are merely part, but not all of the embodiments of the present disclosure. All other embodiments derived by those skilled in the art without creative effort, based on the following embodiments, are within the scope of the present disclosure.

In the present disclosure, the terms "first," "second," and the like are merely used for description, and are not to be construed to indicate or imply any relative importance, or implicitly indicate the number of indicated technical features. Thus, a feature defined with "first" and "second" may expressly or implicitly indicate that one or more features are included. Unless expressly specified, the term "a plurality of" means two or more.

The following description is presented to enable those skilled in the art to implement and use the disclosure. In the following description, details are set forth for explanation. Persons of ordinary skill in the art may recognize that the present disclosure may be implemented without these specific details. In other embodiments, well-known structures and processes may not be described in detail to avoid unnecessarily obscuring the description of the present disclosure. Thus, the present disclosure is not intended to limit the embodiments, but the embodiments consistent with the widest scope of the principles and features disclosed in the present disclosure.

In a current x-ray imaging system, the body of a patient (e.g., a head, a chest, an abdomen, and the like) is scanned with an x-ray tube with a fixed tube voltage and tube current, and the body of the patient is scanned through the x-ray tube to reconstruct an x-ray image of the body of the patient. However, the body sizes of different patients are different, and the attenuation of the angle direction of the body of different patients are also different. Therefore, the fixed tube voltage and tube current may cause excessive radiation dose accepted by some patient to harm the body, or, the fixed tube voltage and tube current may cause insufficient radiation dose accepted by some patient, so as to make that the x-ray cannot pass be through the body of the patient and cannot accurately image.

The embodiments of the present disclosure provide a method for determining tube electrical parameters, a host device, and an imaging system, which are described hereinafter.

Figure 1:
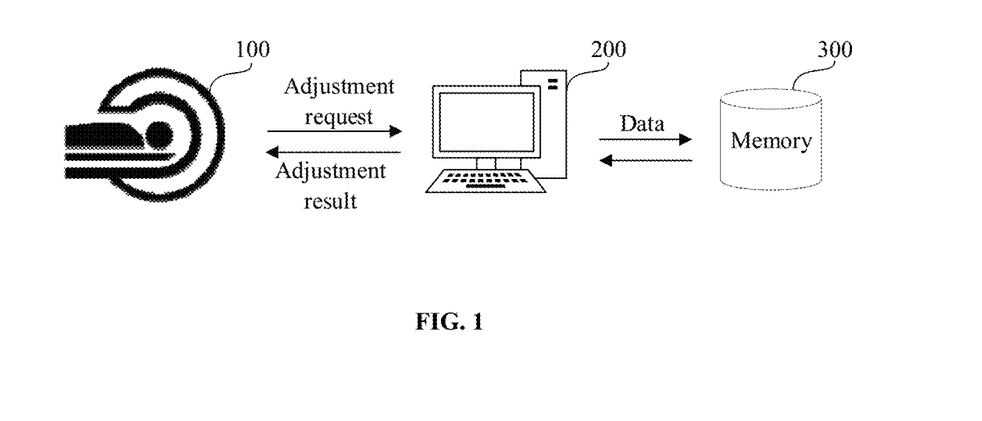
FIG. 1 is a schematic diagram of an imaging system according to an embodiment of the present disclosure.

Referring to FIG. 1, FIG. 1 is a schematic diagram of a scene of an imaging system according to an embodiment of the present disclosure, and the imaging system may be a medical imaging system. The imaging system includes an imaging device 100 and a host device 200, and the imaging device 100 is communicatively connected to the host device 200. The imaging device 100 may transmit data (e.g., projection data) to the host device 200, and the imaging device 100 may acquire medical image of the human body and output the medical image of the human body to the host device 200. The host device 200 is integrated with an apparatus for determining tube electrical parameters, and the apparatus for determining the tube electrical parameters may determine, based on the medical image output by the imaging device 100 to the host device 200, the tube electrical parameters of the imaging device 100 in scanning a target object.

In some embodiments, the imaging system is a radiotherapy system, and the imaging device 100 and a radiotherapy head may be integrated on a rotating carrier. For example, the rotating carrier is a rotating gantry.

In the embodiments of the present disclosure, the imaging device 100 may be a cone beam computed tomography (CBCT) device. In some embodiments, the imaging device 100 includes one tube and one detector, and the detector may be a flat plate detector. In some embodiments, the imaging device 100 includes two groups of tubes and detectors that are arranged orthogonally. The imaging device 100 may further be a computed tomography (CT) device or other imaging device, and the like, which is not limited herein.

In the embodiments of the present disclosure, the host device 200 may be an independent server, or may be a server network or a server cluster of servers. For example, the host device 200 includes, but is not limited to, a computer, a network host device, a single network server, a plurality of network server sets, or a cloud server composed of a plurality of servers. The cloud server is composed of a large number of computers or network servers based on cloud computing.

In the embodiments of the present disclosure, the host device 200 may be a general-purpose computer device, or a special-purpose computer device. The host device 200 may be a desktop computer, a laptop computer, a plurality of server, a personal digital assistant (PDA), a mobile phone, a tablet computer, a wireless terminal device, a communication device, an embedded device, or the like, and the type of the host device 200 is not limited in the embodiments of the present disclosure.

In the embodiments of the present disclosure, the imaging device 100 may be communicated to the host device 200 in any communication fashion, and the communication fashion includes, but is not limited to, a 3rd Generation Partnership Project (3GPP), a Long Term Evolution (LTE), a Worldwide Interoperability for Microwave Access (WiMAX), or a TCP/IP Protocol Suite (TCP/IP), a User Datagram Protocol (UDP), and the like.

The application environment shown in FIG. 1 is only one application scene of the present disclosure, and does not constitute a limitation of the application scene of the present disclosure. Other application environments may also include more or fewer computer devices than those shown in FIG. 1. For example, FIG. 1 merely shows one computer device, and the imaging system may further include one or more other computer devices that may process data, which is not limited herein.

In addition, as shown in FIG. 1, the imaging system may further include a memory 300 configured to store data, such as different tube electrical parameters at a plurality of scan angles, or projection data of the target object, and the like.

The diagram of the scene of the imaging system shown in FIG. 1 is merely one example. The imaging system described in the embodiments of the present disclosure is for a more clear description of the technical solutions of the embodiments of the present disclosure, and does not constitute a limitation of the technical solutions in the embodiments of the present disclosure. The technical solutions in the embodiments of the present disclosure are still applicable to technical problems with the evolution of the imaging system and the appearance of new application scene.

A method for determining tube electrical parameters is provided in the embodiments of the present disclosure. The method includes: acquiring target projection data of an imaging device in scanning a target object at a first scan angle; acquiring target noise data corresponding to the target object; determining current noise data corresponding to the target projection data; and determining, based on the target noise data and the current noise data, the tube electrical parameters of the imaging device in scanning the target object at a second scan angle.

Figure 2:
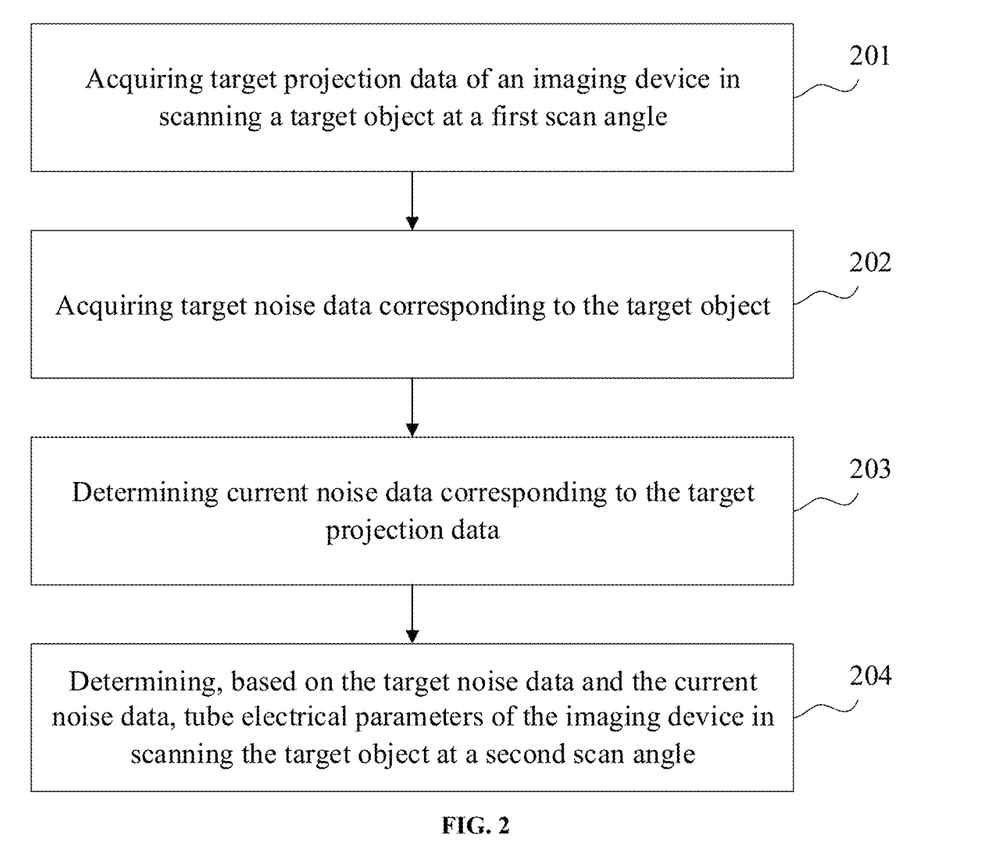
FIG. 2 is a flowchart of a method for determining tube electrical parameters according to an embodiment of the present disclosure.

As shown in FIG. 2, FIG. 2 is a flowchart of a method for determining tube electrical parameters according to an embodiment of the present disclosure. The method may be performed by an apparatus for determining tube electrical parameters, and the apparatus for determining the tube electrical parameters may be integrated in the host device 200. The method for determining the tube electrical parameters includes the processes S201 to S204.

In S201, target projection data of an imaging device in scanning a target object at a first scan angle is acquired.

The target object may be a target point, a target area, or other area referring to body of the patient.

The scan angle is an angle between the imaging device and a preset reference object, and the preset reference object may be the horizon of the ground, a tangent plane of the target object, the horizontal plane of the object carrying the target object, and the like. The scan angle may also be the angle of rotation of the rotating carrier carrying the imaging device, which is not limited herein.

In some embodiments, the scan angle may be a preset angle value, such as 1, 5, or 10 degrees. The scan angle may also be an angle value selected in real time in the scan process.

In S202, target noise data corresponding to the target object is acquired.

Acquiring the target noise data corresponding to the target object may be: acquiring reconstructed projection data by reconstructing the target projection data; determining, an image quality requirement of the target object based on the reconstructed projection data; and determining target noise data corresponding to the target object based on the image quality requirement. The target noise data is used to assess whether current noise data meets a noise level of the clinical diagnostic requirement. Different target objects have different image quality requirements for different inspection purposes, and thus, the target noise data meeting different image quality requirements are also different. For example, in the case that the target object is the head of the patient, the data value of the target noise data of the head with respect to other parts (e.g., the chest, the abdomen) is low because the image quality requirement of the head is high.

In S203, current noise data corresponding to the target projection data is determined.

The current noise data is used to represent the noise level of the target projection data at the current scan angle. Determining the current noise data corresponding to the target projection data may be: acquiring the current noise data corresponding to the target projection data by estimating the noise of the target projection data.

The method for estimating the noise of the target projection data may include a Fourier transformation noise estimation method, a noise estimation method based on an image uniformity area, an noise estimation method based on filter, a noise estimation method based on transformation extract high frequency components, a patch based noise estimation method, a noise estimation method based on establishing a noise model, and the like, which is not limited herein.

In S204, the tube electrical parameters of the imaging device in scanning the target object at the second scan angle are determined based on the target noise data and the current noise data.

After determining the current noise data corresponding to the target projection data, the tube electrical parameters of the imaging device in scanning the target object at the second scan angle may be determined based on the target noise data and the current noise data. The tube electrical parameters are electrical performance data of the tube, and may include a tube voltage, a tube current, a tube resistance, a tube power, and a tube frequency, and the like. In some embodiments, the tube electrical parameters include the tube voltage and the tube current, or may include the tube current merely.

In some embodiments, the imaging device is a CBCT device.

In the method for determining the tube electrical parameters, the target projection data of the imaging device in scanning the target object at the first scan angle is acquired, the target noise data corresponding to the target object is acquired, the current noise data corresponding to the target projection data is determined, and the tube electrical parameters of the imaging device in scanning the target object at the second scan angle are determined based on the target noise data and the current noise data. In the case of not establishing the knowledge base in advance, suitable tube electrical parameters are selected from the noise data estimated based on the projection data, which increases the quality of the reconstructed image, reduces the radiation dose accepted by the patient, and plays an important role in low dose imaging of the medical imaging device.

In some embodiments, acquiring the target projection data of the imaging device in scanning the target object at the first scan angle may include: acquiring initial projection data of the imaging device in scanning the target object at the first scan angle; and acquiring the target projection data of the imaging device in scanning the target object at the first scan angle by screening the initial projection data. The initial projection data is the projection data directly acquired in the process of the imaging device scanning the target object at the target scan angle.

After acquiring the initial projection data of the imaging device in scanning the target object at the first scan angle, the initial projection data may be screened as the acquired initial projection data is relatively complex. In some embodiments, acquiring the target projection data of the imaging device in scanning the target object at the first scan angle by screening the initial projection data may include acquiring the target projection data of the imaging device in scanning the target object at the first scan angle by screening, based on a preset sliding window parameter, the initial projection data by screening the initial projection data in a step sliding window mode.

The preset sliding window parameter may include a step window width n, a step distance m and a number of the adjustment i, and the like. Screening the initial projection data by screening, based on the preset sliding window parameter, the initial projection data in the step sliding window mode may be screening the initial projection data by screening the initial projection data in the step sliding window mode based on the preset sliding window parameter a formula $1+m*(i-1) \sim n+m*(i-1)$, wherein i is a positive integer.

After acquiring the target projection data, the current noise data of the target projection data may be determined. Determining the current noise data of the target projection data may include: determining a noise component of the target protection data by a spatial transformation on the target projection data; and acquiring the current noise data of the target projection data by a noise estimation on the target projection data based on the noise component.

Determining the noise component of the target protection data by the spatial transformation on the target projection data may be: determining a three-dimension Fourier space of the target projection data by a Fourier spatial transformation on the target projection data; and acquiring the noise component of the target projection data by decoupling the noise component and the signal component of the target projection data based on the three-dimension Fourier space.

In the method for determining the tube electrical parameters in the embodiments of the present disclosure, the target projection data suitable for determining the tube electrical parameters is acquired by screening the initial projection data, the current noise data of the target projection data is determined based on the noise component of the target projection data, and the tube electrical parameters of the imaging device in scanning the target object at a second scan angle are determined based on the target projection data and the current noise data. Thus, the accuracy of determining the tube electrical parameters is improved.

In some embodiments, determining, based on the target noise data and the current noise data, the tube electrical parameters of the imaging device in scanning the target object at the second scan angle may include: determining, based on the target noise data, the current noise data, and a first correspondence relationship, the target tube electrical parameters in scanning the target object, wherein the first correspondence relationship includes a correspondence relationship between the noise data and the target tube electrical parameters; and determining, based on the target tube electrical parameters, the tube electrical parameters of the imaging device in scanning the target object at the second scan angle.

In some embodiments, prior to determining the target tube electrical parameters in scanning the target object based on the target noise data, the current noise data, and the first correspondence relationship, the method further includes establishing the first correspondence relationship.

In some embodiments, the first correspondence relationship is a correspondence relationship of noise data, an equivalent size, and the tube electrical parameters. The equivalent size is the size of the equivalent material for simulating the target object in the scanning process, and the equivalent size is a length of the equivalent attenuation path of the scanned object at an angle. For example, the equivalent material may be water that is very close to the human body density. For the equivalent size of the human body, $\int u_{human\ body}(z)dz = u_{water}$*the equivalent size, wherein u represents a linear attenuation coefficient of the material (e.g., the water or the human body), and z represents the attenuation path of the x-ray.

In some embodiments, establishing the first correspondence relationship may include acquiring the noise data under different equivalent sizes and different tube electrical parameters; and establishing the first correspondence relationship based on the noise data under the different equivalent sizes and the different tube electrical parameters. For example, the first correspondence relationship is acquired by a data augmentation on the noise data under the different equivalent sizes and the different tube electrical parameters.

The data augmentation may be an interpolation operation, a fitting operation, or other data augmentation method, which is not limited herein.

It is noted that the target object has the equivalent size corresponding to each scan angle, and the equivalent size corresponding to each scan angle is the length of the equivalent attenuation path at each scan angle.

In some embodiments, the first correspondence relationship is the correspondence relationship of the noise data, the equivalent size, and the tube electrical parameters; and determining, based on the target noise data, the current noise data, and the first correspondence relationship, the target tube electrical parameters in scanning the target object may include: acquiring current tube electrical parameters of the imaging device at the first scan angle; determining the equivalent size of the target object based on the current noise data, the current tube electrical parameters, and the first correspondence relationship; and determining, based on the equivalent size of the target object and the target noise data, the target tube electrical parameters in scanning the target object.

In some embodiments, determining, based on the equivalent size of the target object and the target noise data, the target tube electrical parameters in scanning the target object may include: determining, based on the equivalent size of the target object, the target noise data, and the first correspondence relationship, a set of the tube electrical parameters that match the target noise data and the equivalent size of the target object; and determining the tube electrical parameters in scanning the target object from the set of the tube electrical parameters.

In some embodiments, the tube electrical parameters include the tube current and the tube voltage; and determining the target tube electrical parameters in scanning the target object from the set of the tube electrical parameters may include: determining a dose value corresponding to each of the tube electrical parameters in the set of the tube electrical parameters; and selecting the tube electrical parameters corresponding to a minimum dose value in the set of the tube electrical parameters to act as the target tube electrical parameters in scanning the target object.

Taking the equivalent size being d, the tube electrical parameters including the tube voltage U and the tube current I, and the noise data being $\sigma^2$ as an example, and the correspondence relationship of the noise data and the tube electrical parameters is shown in Table 1. Assuming that the current tube voltage U of the imaging device at the first scan angle is 80, the current tube current I of the imaging device at the first scan angle is 100, the current noise data $\sigma^2$ of the imaging device at the first scan angle is 20, and the target noise data $\sigma^2$ is 10, the equivalent size d of the target object is determined to be 300 based on the current voltage U being 80, the current tube current I being 100, the current noise data being 20, and Table 1, and the set of the tube electrical parameters that match the target noise data being 10 are determined based on the equivalent size d of the target object and the target noise data $\sigma^2$, and Table 1. There are two sets, one set is a set of the tube voltage U being 100 and the tube current I being 70, the other set is a set of the tube voltage U being 120 and the tube current I being 50. In the above two sets of tube electrical parameters, the target tube electrical parameters corresponding to the target noise data are determined.

TABLE 1

| Equivalent size d(mm) | Tube voltage U(kv) | Tube current I(mA) | Noise data $\sigma^2$ |
|---|---|---|---|
| 300 | 80 | 100 | 20 |
| 300 | 100 | 70 | 10 |
| 300 | 120 | 50 | 10 |

Table 1 is merely exemplary, and in other embodiments, there may be more equivalent size, noise data, and tube electrical parameters, which are not limited herein.

The first correspondence relationship in the embodiments of the present disclosure shows the correspondence relationship of the target object at different scan angles, different tube electrical parameters, and different noise data, and thus, the adjustment mode of the tube electrical parameters can be determined based on the noise data, thereby reducing the radiation dose accepted by the patient in the scan process.

In addition to determining the target tube electrical parameters corresponding to the target noise data by the first correspondence relationship and determining the tube electrical parameters of the imaging device in scanning the target object at the second scan angle based on the target tube electrical parameters, the tube electrical parameters of the imaging device in scanning the target object at the second scan angle may be determined in other mode.

For example, the tube electrical parameters include a tube current and a tube voltage, the tube current being adjustable and the tube voltage being constant. Determining, based on the target noise data and the current noise data, the tube electrical parameters of the imaging device in scanning the target object at the second scan angle may include: acquiring the current tube current of the imaging device in scanning the target object at the first scan angle; and determining, based on the target noise data, the current noise data and the current tube current, the tube current of the imaging device in scanning the target object at a second scan angle.

Acquiring the current tube current of the imaging device in scanning the target object at the first scan angle may be directly acquiring the current tube current of the imaging device in scanning the target object at the first scan angle in the case that the tube voltage is a fixed value.

In some embodiments, determining, based on the target noise data, the current noise data and the current tube current, the tube current of the imaging device in scanning the target object at a second scan angle may be: acquiring a noise ratio of the first scan angle by computing the target noise data and the current noise data (e.g., determining a ratio of the target noise data and the current noise data, and determining the ratio as the noise ratio of the first scan angle); determining, based on the noise ratio and the current tube current, the tube current of the imaging device in scanning the target object at a second scan angle.

In some embodiments, taking the target noise data being $\sigma_{obj}^2$ and the current noise data being $\sigma_{est}^2$ as an example, the noise ratio of the first scan angle may be $\sigma_{obj}^2/\sigma_{est}^2$. Assuming that the current tube current is I, the tube current in scanning the target object at the second scan angle is $I_{new}=(\sigma_{obj}^2/\sigma_{est}^2)*I$, that is, the tube current in scanning the target object at a second scan angle may be determined based on a ratio of the target noise data to the current noise data, and the current tube current in the case that the tube voltage is a fixed value.

In the method for determining the tube electrical parameters in the embodiments of the present disclosure, provided is a method for adjusting the tube current in the case that the tube voltage is a fixed value. Based on the ratio of the target noise data to the current noise data, the tube current of scanning the target object at the next angle can be determined directly and quickly, the quality of imaging and the accuracy of scanning are ensured, and various methods for determining the tube electrical parameters are provided.

In some embodiments, the tube electrical parameters include the tube current and the tube voltage, the tube current being adjustable and the tube voltage being constant, and determining, based on the target noise data and the current noise data, the tube electrical parameters of the imaging device in scanning the target object at the second scan angle includes: acquiring a current tube current of the imaging device in scanning the target object at the first scan angle; and determining, based on the target noise data, the current noise data and the current tube current, the tube current of the imaging device in scanning the target object at the second scan angle.

In some embodiments, determining, based on the target noise data, the current noise data and the current tube current, the tube current of the imaging device in scanning the target object at the second scan angle may include determining, based on the target noise data and the current noise data, the tube current of the imaging device in scanning the target object at the second scan angle in the case that when the current noise data exceeds the preset noise data. The preset noise data may be the target noise data, or other data with a preset noise value, such as 10 dB, 15 dB, 20 dB, or the like.

In some embodiments, for some clinical scene, a scan of the diagnostic CT may be performed prior to performing the CBCT scan, and the method for determining the tube electrical parameters may be: acquiring the target projection data of the imaging device in scanning the target object at the first scan angle; determining a planned angle of the target object based on the projection data; acquiring, based on the projection data corresponding to the planned angle, angle noise data of the target object by a noise estimation; acquiring simulated projection data of the target object by simulating projection data of the imaging device in scanning the target object at the first scan angle; establishing, based on the simulated projection data, a correspondence relationship of the noise data and the tube electrical parameters; determining, based on the angle noise data and the correspondence relationship of the noise data and the tube electrical parameters, the tube electrical parameters of the imaging device in scanning the target object at the second scan angle.

In the method for determining the tube electrical parameters in the embodiments of the present disclosure, the noise of the completely scanned projection data is estimated in advance, and the change of the tube electrical parameters in the scanning process is determined in advance. Thus, the uncertainty in adjusting the tube electrical parameters in the scanning process is reduced, and the quality of medical imaging is ensured.

In some clinical scene, a diagnostic scan may be performed prior to a scan by a medical device (e.g., CBCT) to acquire complete projection data. For example, the diagnostic scan may be performed through the CT device to obtain the complete projection data of the target object acquired in the diagnostic scan process. The scan angle may be divided into m scan angle ranges (m is a positive integer) based on the complete projection data, and the noise level of the projection data within each scan angle range is estimated. The tube electrical parameters of the imaging device in scanning the target object within each scan angle range are determined based on the dose level plan planned before the scan, thereby acquiring the tube electrical parameters of the imaging device in scanning the target object at each scan angle. The method may estimate the noise level of the completely scanned projection data in advance, and determine the variation of the tube electrical parameters prior to the present scan operation in advance.

Figure 3:
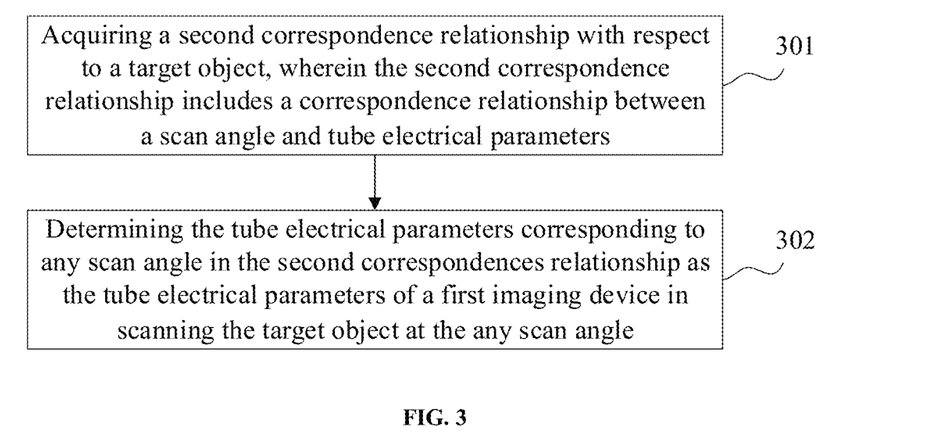
FIG. 3 is a flowchart of another method for determining tube electrical parameters according to an embodiment of the present disclosure.

As shown in FIG. 3, FIG. 3 is a flowchart of another method for determining tube electrical parameters according to an embodiment of the present disclosure. The method may be performed by an apparatus for determining the tube electrical parameters, and the apparatus may be integrated in the host device 200. The method for determining the tube electrical parameters includes the processes S301 to S302.

In S301, a second correspondence relationship with respect to a target object is determined, wherein the second correspondence relationship includes a correspondence relationship between a scan angle and the tube electrical parameters.

The target object may be a target point, a target area, or other area referring to body of the patient.

The scan angle is an angle between the imaging device and a preset reference object, and the preset reference object may be the horizon of the ground, a tangent plane of the target object, the horizontal plane of the object carrying the target object, and the like.

In some embodiments, the scan angle may be a preset angle value, such as 1, 5, or 10 degrees. The scan angle may also be an angle value selected in real time in the scan process.

In S302, the tube electrical parameters corresponding to any scan angle in the second correspondences relationship are determined as the tube electrical parameters of a first imaging device in scanning the target object at the any scan angle.

After acquiring the second correspondence relationship with respect to the target object, the tube electrical parameters of the first imaging device in scanning the target object at each scan angle may be determined based on the second correspondence relationship in the actual scan process. For example, the tube electrical parameters corresponding to any scan angle in the second correspondence relationship may be determined as the tube electrical parameters of the first imaging device in scanning the target object at the any scan angle. That is, the tube electrical parameters corresponding to any scan angle recorded in the second correspondence are determined as the tube electrical parameters of the first imaging device in scanning the target object at the any scan angle.

In the method for determining the tube electrical parameters in the embodiments of the present disclosure, the second correspondence relationship with respect to the target object is determined, wherein the second correspondence relationship includes the correspondence relationship between the scan angle and the tube electrical parameters. The tube electrical parameters of the first imaging device in scanning the target object at each scan angle are determined based on the second correspondence relationship in the actual scan process. Thus, The tube electrical parameters of the first imaging device in scanning the target object at different scan angle may be different, which may prevent excessive radiation dose accepted by some patient from harming the body, or prevent insufficient radiation dose accepted by some patient from inaccurately imaging.

In some embodiments, prior to acquiring the second correspondence relationship, the method further includes establishing the second correspondence relationship.

In some embodiments, establishing the second correspondence relationship includes: acquiring projection data of a second imaging device in scanning the target object at different scan angles; acquiring target noise data corresponding to the target object; determining noise data corresponding to the projection data at the different scan angles; determining, based on the noise data corresponding to the projection data at the different scan angles and the target noise data, the tube electrical parameters of the second imaging device in scanning the target object at different scan angles; and establishing the second correspondence relationship based on the tube electrical parameters of the second imaging device in scanning the target object at the different scan angles.

In some embodiments, the first imaging device is the CBCT device, and the second imaging device is the CT device. The projection data of the second imaging device in scanning the target object at different scan angles may be the complete projection data of the second imaging device for acquiring the target object in the diagnostic process. For example, the CT device acquires the complete projection data of the target object in the diagnostic process.

Figure 4:
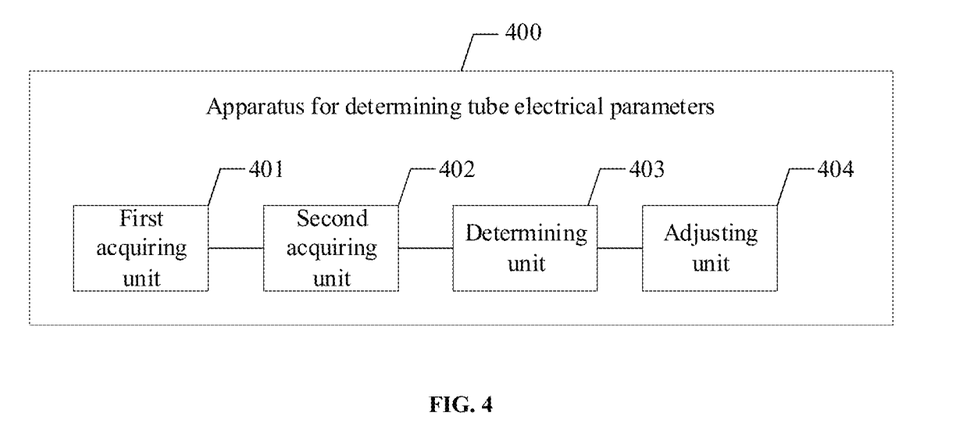
FIG. 4 is a schematic structural diagram of an apparatus for determining tube electrical parameters according to an embodiment of the present disclosure.

Based on the method for determining the tube electrical parameters, the apparatus 400 for determining tube electrical parameters is further provided in the embodiments of the present disclosure. As shown in FIG. 4, the apparatus 400 includes:

a first acquiring unit 401 configured to acquire target projection data of an imaging device in scanning a target object at a first scan angle;

a second acquiring unit 402 configured to acquire target noise data corresponding to the target object;

a determining unit 403 configured to determine current noise data corresponding to the target projection data; and an adjusting unit 404 configured to determine, based on the target noise data and the current noise data, the tube electrical parameters of the imaging device in scanning the target object at a second scan angle.

In some embodiments, the first acquiring unit 401 is further configured to:

acquire initial projection data of the imaging device in scanning the target object at the first scan angle; and acquire the target projection data by screening the initial projection data.

In some embodiments, the first acquiring unit 401 further configured to screen, based on a preset sliding window parameter to acquire the target projection data, the initial projection data in a step sliding window mode.

In some embodiments, the determining unit 403 is further configured to:

determine a noise component of the target projection data by a spatial transformation on the target projection data; and acquire the current noise data of the target projection data by a noise estimation on the target projection data based on the noise component.

In some embodiments, the adjusting unit 404 is further configured to:

determine, based on the target noise data, the current noise data, and a first correspondence relationship, target tube electrical parameters in scanning the target object, wherein the correspondence relationship includes a correspondence relationship between the noise data and the tube electrical parameters; and determine, based on the target tube electrical parameters, the tube electrical parameters of the imaging device in scanning the target object at the second scan angle.

In some embodiments, the adjusting unit 404 is further configured to:
acquire current tube electrical parameters of the imaging device at the first scan angle;
determine the equivalent size of the target object based on the current noise data, the current tube electrical parameters, and the first correspondence relationship; and
determine, based on the equivalent size of the target object and the target noise data, the target tube electrical parameters in scanning the target object.

In some embodiments, the adjusting unit 404 further configured to:
determine, based on the equivalent size of the target object, the target noise data, and the first correspondence relationship, a set of the tube electrical parameters that match the target noise data and the equivalent size of the target object; and
determine the target tube electrical parameters in scanning the target object from the set of the tube electrical parameters.

In some embodiments, the adjusting unit 404 is further configured to:
determine a dose value corresponding to each tube electrical parameters in the set of the tube electrical parameters; and
select the tube electrical parameters corresponding to a minimum dose value in the set of the tube electrical parameters to act as the target tube electrical parameters in scanning the target object.

In some embodiments, the tube electrical parameters includes a tube current and a tube voltage.

In some embodiments, the tube current being adjustable and the tube voltage being constant, and the adjusting unit 404 is further configured to:
acquire a current tube current of the imaging device in scanning the target object at the first scan angle;
determine, based on the target noise data, the current noise data and the current tube current, the tube current of the imaging device in scanning the target object at a second scan angle.

In some embodiments, the adjusting unit 404 is further configured to determine, based on the target noise data and the current noise data, the tube electrical parameters of the imaging device in scanning the target object at the second scan angle in the case that the current noise data exceeds a preset noise data.

In the apparatus for determining the tube electrical parameters, the target projection data of the imaging device in scanning the target object at the first scan angle is acquired, the target noise data corresponding to the target object is acquired, the current noise data corresponding to the target projection data is determined, and the tube electrical parameters of the imaging device in scanning the target object at the second scan angle is determined based on the target noise data and the current noise data. In the case of not establishing the knowledge base in advance, a suitable tube electrical parameters is selected from the noise data estimated based on the projection data, which increases the quality of the reconstructed image, reduces the radiation dose accepted by the patient, and plays an important role in low dose imaging of the medical imaging device.

Figure 5:
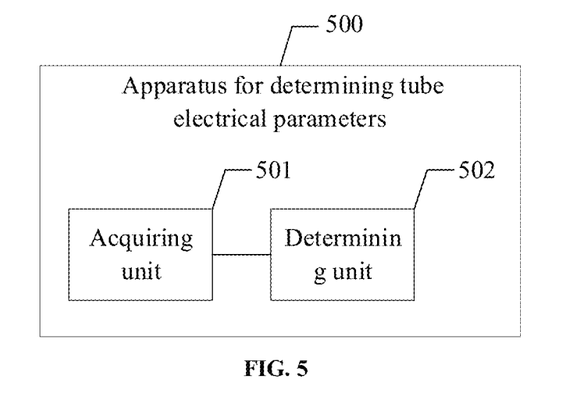
FIG. 5 is a schematic structural diagram of another apparatus for determining tube electrical parameters according to an embodiment of the present disclosure.

Based on the method for determining the tube electrical parameters, an apparatus 500 for determining tube electrical parameters is also provided in the embodiments of the present disclosure. As shown in FIG. 5, the apparatus includes:
an acquiring unit 501 configured to acquire a second correspondence relationship with respect to a target object, wherein the second correspondence relationship includes a correspondence relationship between a scan angle and the tube electrical parameters; and
a determining unit 502 configured to determine the tube electrical parameters corresponding to any scan angle in the second correspondences relationship as the tube electrical parameters of a first imaging device in scanning the target object at the any scan angle.

In the apparatus for determining the tube electrical parameters in the embodiments of the present disclosure, the second correspondence relationship with respect to the target object is acquired, wherein the second correspondence relationship includes the correspondence relationship between the scan angle and the tube electrical parameters. The tube electrical parameters of the first imaging device in scanning the target object at different scan angle are determined based on the second correspondence relationship in the actual scan process. Thus, The tube electrical parameters of the first imaging device in scanning the target object at different scan angle may be different, which may prevent excessive radiation dose accepted by some patient from harming the body, or prevent insufficient radiation dose accepted by some patient from inaccurately imaging.

In some embodiments, the apparatus further includes an establishing unit configured to establish the second correspondence relationship prior to the acquiring unit 501 acquiring the second correspondence relationship with respect to the target object.

In some embodiments, the establishing unit is further configured to perform:
acquiring projection data of a second imaging device in scanning the target object at different scan angles;
acquiring target noise data corresponding to the target object;
determining noise data corresponding to the projection data at the different scan angles;
determining, based on the noise data corresponding to the projection data at the different scan angles and the target noise data, the tube electrical parameters of the second imaging device in scanning the target object at different scan angles; and
establishing the second correspondence relationship based on the tube electrical parameters of the second imaging device in scanning the target object at the different scan angles.

In some embodiments, the second imaging device is a CT device.

A host device is further provided in the embodiments of the present disclosure, and the host device is integrated with the apparatus 400 or apparatus 500 described above. The host device includes:
one or more processors;
a memory configured to store one or more computer programs therein; and
wherein the one or more processors, when loading and running the one or more computer programs, are caused to perform the method in the embodiments described above.

Figure 6:
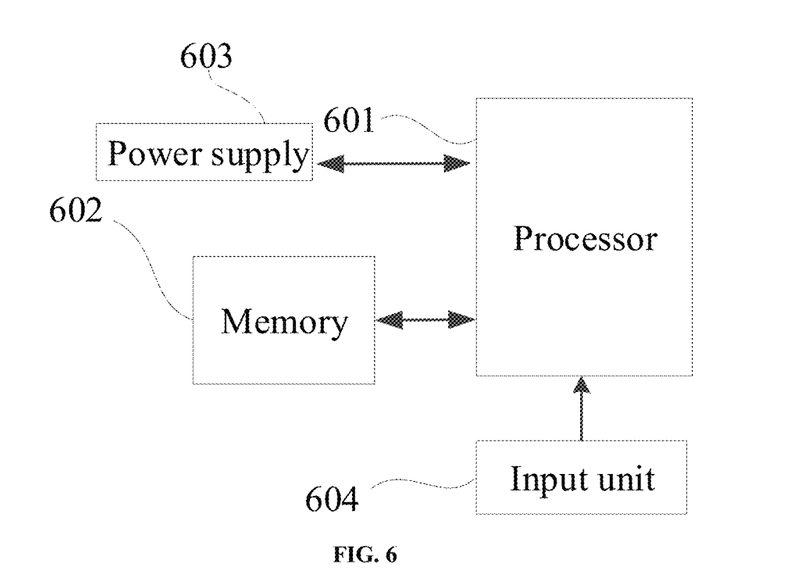
FIG. 6 is a schematic structural diagram of a host device according to an embodiment of the present disclosure.

As shown in FIG. 6, FIG. 6 is a schematic structural diagram of a host device according to an embodiment of the present disclosure. The host device includes a processor 601 including one or more processing cores, one or more memories 602, a power supply 603, an input unit 604, and the like. The host device structure shown in FIG. 6 does not constitute a limitation of the host device, and the host device may include more or fewer components compared with the structure shown in FIG. 6, a combination of some components, or different arrangements of the components.

The processor 601 is a control center of the host device, and the processor 601 is connected to portions of the host device by various interfaces and/or lines. The processor 601 performs various functions of the host device and data processing by running or executing software programs and/or modules stored in the memory 602 and calling data stored in the memory 602, so as to monitor the host device overall. In some embodiments, the processor 601 includes one or more processing cores. The processor 601 may be a central processing unit (CPU), other general-purpose processor, a digital signal processor (DSP), an application specific integrated circuit (ASIC), a field-programmable gate array (FPGA), other programmable logic device, discrete gate or transistor logic, and discrete hardware components, or the like. The general-purpose processor may be a microprocessor, any conventional processor, or the like. The processor 601 may be an integrated with an application processor and a modem processor, the application processor primarily processes the operating system, user interfaces, the application, and the like, and the modem processor primarily processes the wireless communication. It is noted that the modem processor may also not be integrated into the processor 601.

The memory 602 may be configured to store one or more computer programs therein, and the processor 601 executes various functional application and data processing by running the software programs and the modules stored in the memory 602. The memory 602 may include a storage program area and a storage data area. The storage program area may store an operation system, the application required by at least one function (such as a sound playing function, an image playing function, and the like), and the like. The storage data area may store data created based on the use of the host device, or the like. Furthermore, the memory 602 may include a high-speed random access memory, and may further include a non-volatile memory. For example, the memory 602 may include at least one of a magnetic disk storage device, a flash memory device, or other volatile solid state storage device. Correspondingly, the memory 602 may further include a memory controller to provide access of the memory 602 by the processor 601.

The power supply 603 is configured to supply power to the components of the host device, and the power supply 603 may be logically connected to the processor 601 through a power management system to achieve management of functions such as charging, discharging, and power consumption management through the power management system. The power supply 603 may include one or more of a direct current or alternating current power supply, a recharging system, a power failure detection circuit, a power converter or inverter, a power status indicator, and the like.

The input unit 604 may be configured to receive input digital or character information, and produce a keyboard, a mouse, a joystick, an optical or trackball signal input related to user settings and functional controls.

Although not shown, the host device may also include a display unit or the like, which is not repeated herein. Particularly, in the embodiments, the processor 601 in the host device may load the executable files corresponding to the processes of one or more computer programs into the memory 602 and run the one or more computer programs stored in the memory 602 to achieve various functions by:

acquiring target projection data of an imaging device in scanning a target object at a first scan angle;

acquiring target noise data corresponding to the target object;

determining current noise data corresponding to the target projection data; and     determining, based on the target noise data and the current noise data, the tube electrical parameters of the imaging device in scanning the target object at a second scan angle.

In some embodiments, an imaging system is further provided in the embodiments of the present disclosure. The imaging system includes a host device and an imaging device, and the host device is communicatively connected to the imaging device. The host device is the host device described in the embodiments described above, and the imaging device is the imaging device described in other embodiments of the present disclosure.

Those of ordinary skill in the art may understand that all or part of the processes of the various methods of the embodiments described above may be performed by instructions, or a related hardware controlled by the instruction, and the instruction may be stored in a computer-readable storage medium, and loaded and executed by a processor.

In addition, a computer-readable storage medium is provided in the embodiments of the present disclosure. The computer-readable storage medium may include a read-only memory (ROM), a random-access memory (RAM), a magnetic, an optical disk, and the like. The computer-readable storage medium stores one or more computer program. The one or more computer programs, when loaded and run by a processor of an electronic device, causes the electronic device to perform the method for determining the tube electrical parameters described in the embodiments of the present disclosure. For example, the computer program, when loaded and run by a processor, causes the processor to perform:

acquiring target projection data of an imaging device in scanning a target object at a first scan angle;

acquiring target noise data corresponding to the target object;

determining current noise data corresponding to the target projection data; and     determining, based on the target noise data and the current noise data, the tube electrical parameters of the imaging device in scanning the target object at a second scan angle.

In the above embodiments, descriptions of various embodiments focus on different aspects, and the process not detailed in the embodiment may be referred to the description in other embodiments described above, which is not repeated herein.

In a specific implementation, the various units or structures described above may be implemented as separate entities, or may be combined in any combination to be implemented as a single entity or multiple entities. The implementations of the various units or structures described above may be referred to the foregoing embodiments, which are not repeated herein.

Detailed descriptions of the various operations above may be referred to the foregoing embodiments, which are not repeated herein.

The method for determining tube electrical parameters, the host device, and the imaging system are described in the above embodiments of the present disclosure, and the principles and embodiments of the present disclosure are illustrated herein with specific embodiments. The description of the above embodiments merely helps to understand the method and the core idea in the present disclosure. Meanwhile, the implementations and the scope may be changed for those skilled in the art based on the concepts of the present disclosure, and thus, the present specification should not be construed as a limitation of the present disclosure.

What is claimed is:

1. A method for determining tube electrical parameters, comprising:
   acquiring target projection data of an imaging device in scanning a target object at a first scan angle;
   acquiring target noise data corresponding to the target object;
   determining current noise data corresponding to the target projection data; and
   determining, based on the target noise data and the current noise data, the tube electrical parameters of the imaging device in scanning the target object at a second scan angle;
   wherein the tube electrical parameters comprise a tube current and a tube voltage, the tube current being adjustable and the tube voltage being constant, and
   wherein determining, based on the target noise data and the current noise data, the tube electrical parameters of the imaging device in scanning the target object at the second scan angle comprises:
      acquiring a current tube current of the imaging device in scanning the target object at the first scan angle;
      determining a ratio of the target noise data and the current noise data as a noise ratio of the first scan angle; and
      using a product of the noise ratio and the current tube current as the tube current of the imaging device in scanning the target object at the second scan angle.

2. The method according to claim 1, wherein the imaging device is a cone beam computed tomography (CBCT) device.

3. The method according to claim 1, wherein acquiring the target projection data of the imaging device in scanning the target object at the first scan angle comprises:
   acquiring initial projection data of the imaging device in scanning the target object at the first scan angle; and
   acquiring the target projection data by screening the initial projection data.

4. The method according to claim 3, wherein screening the initial projection data comprises:
   screening, based on a preset sliding window parameter, the initial projection data in a step sliding window mode.

5. The method according to claim 1, wherein determining the current noise data corresponding to the target projection data comprises:
   determining a noise component of the target projection data by a spatial transformation on the target projection data; and
   acquiring the current noise data of the target projection data by a noise estimation on the target projection data based on the noise component.

6. The method according to claim 1, wherein determining, based on the target noise data and the current noise data, the tube electrical parameters of the imaging device in scanning the target object at the second scan angle comprises:
   determining, based on the target noise data, the current noise data, and a first correspondence relationship, target tube electrical parameters in scanning the target object, wherein the first correspondence relationship comprises a correspondence relationship between the noise data and the tube electrical parameters; and
   determining, based on the target tube electrical parameters, the tube electrical parameters of the imaging device in scanning the target object at the second scan angle.

7. The method according to claim 6, wherein prior to determining, based on the target noise data, the current noise data, and the first correspondence relationship, the target tube electrical parameters in scanning the target object, the method further comprises:
   establishing the first correspondence relationship.

8. The method according to claim 7, wherein
   the first correspondence relationship is a correspondence relationship of noise data, an equivalent size, and the tube electrical parameters; and
   establishing the first correspondence relationship comprises:
      acquiring the noise data under different equivalent sizes and different tube electrical parameters; and
      establishing the first correspondence relationship based on the noise data under the different equivalent sizes and the different tube electrical parameters.

9. The method according to claim 8, wherein establishing the first correspondence relationship based on the noise data under the different equivalent sizes and the different tube electrical parameters comprises:
   acquiring the first correspondence relationship by a data augmentation on the noise data under the different equivalent sizes and the different tube electrical parameters.

10. The method according to claim 8, wherein determining the target tube electrical parameters in scanning the target object based on the target noise data, the current noise data, and the first correspondence relationship comprises:
    acquiring current tube electrical parameters of the imaging device at the first scan angle;
    determining the equivalent size of the target object based on the current noise data, the current tube electrical parameters, and the first correspondence relationship; and
    determining, based on the equivalent size of the target object and the target noise data, the target tube electrical parameters in scanning the target object.

11. The method according to claim 10, wherein determining, based on the equivalent size of the target object and the target noise data, the target tube electrical parameters in scanning the target object comprises:
    determining, based on the equivalent size of the target object, the target noise data, and the first correspondence relationship, a set of the tube electrical parameters that match the target noise data and the equivalent size of the target object; and
    determining the target tube electrical parameters in scanning the target object from the set of the tube electrical parameters.

12. The method according to claim 11, wherein determining the target tube electrical parameters in scanning the target object from the set of the tube electrical parameters comprises:
    determining a dose value corresponding to each of the tube electrical parameters in the set of the tube electrical parameters; and
    selecting the tube electrical parameters corresponding to a minimum dose value in the set of the tube electrical parameters to act as the target tube electrical parameters in scanning the target object.

13. A non-transitory computer-readable storage medium storing one or more computer programs therein, wherein the one or more computer programs, when loaded and run by a processor of an electronic device, cause the electronic device to perform a method comprising:
   acquiring target projection data of an imaging device in scanning a target object at a first scan angle;
   acquiring target noise data corresponding to the target object;
   determining current noise data corresponding to the target projection data; and
   determining, based on the target noise data and the current noise data, tube electrical parameters of the imaging device in scanning the target object at a second scan angle;
   wherein the tube electrical parameters comprise a tube current and a tube voltage, the tube current being adjustable and the tube voltage being constant, and
   wherein determining, based on the target noise data and the current noise data, the tube electrical parameters of the imaging device in scanning the target object at the second scan angle comprises:
      acquiring a current tube current of the imaging device in scanning the target object at the first scan angle;
      determining a ratio of the target noise data and the current noise data as a noise ratio of the first scan angle; and
      using a product of the noise ratio and the current tube current as the tube current of the imaging device in scanning the target object at the second scan angle.

14. A host device, comprising:
   one or more processors;
   a memory configured to store one or more computer programs therein; and
   wherein the one or more processors, when loading and running the one or more computer programs, are caused to perform a method for determining tube electrical parameters;
   the method comprising:
      acquiring target projection data of an imaging device in scanning a target object at a first scan angle;
      acquiring target noise data corresponding to the target object;
      determining current noise data corresponding to the target projection data; and
      determining, based on the target noise data and the current noise data, the tube electrical parameters of the imaging device in scanning the target object at a second scan angle;
   wherein the tube electrical parameters comprise a tube current and a tube voltage, the tube current being adjustable and the tube voltage being constant, and
   wherein determining, based on the target noise data and the current noise data, the tube electrical parameters of the imaging device in scanning the target object at the second scan angle comprises:
      acquiring a current tube current of the imaging device in scanning the target object at the first scan angle;
      determining a ratio of the target noise data and the current noise data as a noise ratio of the first scan angle; and
      using a product of the noise ratio and the current tube current as the tube current of the imaging device in scanning the target object at the second scan angle.

15. An imaging system, comprising a host device and an imaging device, wherein the host device is communicatively connected to the imaging device, and the host device is the host device as defined in claim 14.

* * * * *